United States Patent [19]

Burgel et al.

[11] Patent Number: 5,245,855
[45] Date of Patent: Sep. 21, 1993

[54] RAIL SEAT ABRASION MEASUREMENT

[75] Inventors: Bill Burgel, West Linn; Erik Roe, Portland, both of Oreg.

[73] Assignee: Rittenhouse-Zemen & Associates, Inc., Portland, Oreg.

[21] Appl. No.: 719,381

[22] Filed: Jun. 24, 1991

[51] Int. Cl.$^5$ .............................................. G01N 3/56
[52] U.S. Cl. ........................................... 73/8; 73/146
[58] Field of Search ............................... 73/8, 7, 146

[56] References Cited

U.S. PATENT DOCUMENTS

| | | | |
|---|---|---|---|
| 3,588,049 | 1/1971 | Pennino | 238/29 |
| 4,018,164 | 4/1971 | Bryan, Jr. | 104/9 |
| 4,326,669 | 4/1982 | Moult et al. | 238/36 |
| 4,925,094 | 5/1990 | Buckett | 238/304 X |

FOREIGN PATENT DOCUMENTS

| | | | |
|---|---|---|---|
| 157655 | 12/1979 | Japan | 73/8 |
| 6103 | 1/1981 | Japan | 73/8 |
| 61908 | 3/1988 | Japan | 73/8 |
| 61909 | 3/1988 | Japan | 73/8 |
| 1179132 | 9/1985 | U.S.S.R. | 73/8 |
| 1237942 | 6/1986 | U.S.S.R. | 73/8 |

Primary Examiner—Tom Noland
Attorney, Agent, or Firm—Robert L. Harrington

[57] ABSTRACT

A method and apparatus for rail seat abrasion measurement and analysis is shown wherein a rail seat measurement device is mounted with reference to non-wear portions of a concrete railroad tie and includes linear potentiometer devices adapted to determine a spacial relationship between the body of the measurement device and wearing portions of the rail seat. In this manner, the measurement device may be consistently mounted upon the non-wear portions of the concrete railroad tie in order that a series of accurate abrasion measurements may be taken. Other information collected includes static information such as track curvature, bank, and grade and dynamic information such as loading conditions and environmental conditions to which the rail seat is exposed between abrasion measurements.

15 Claims, 7 Drawing Sheets

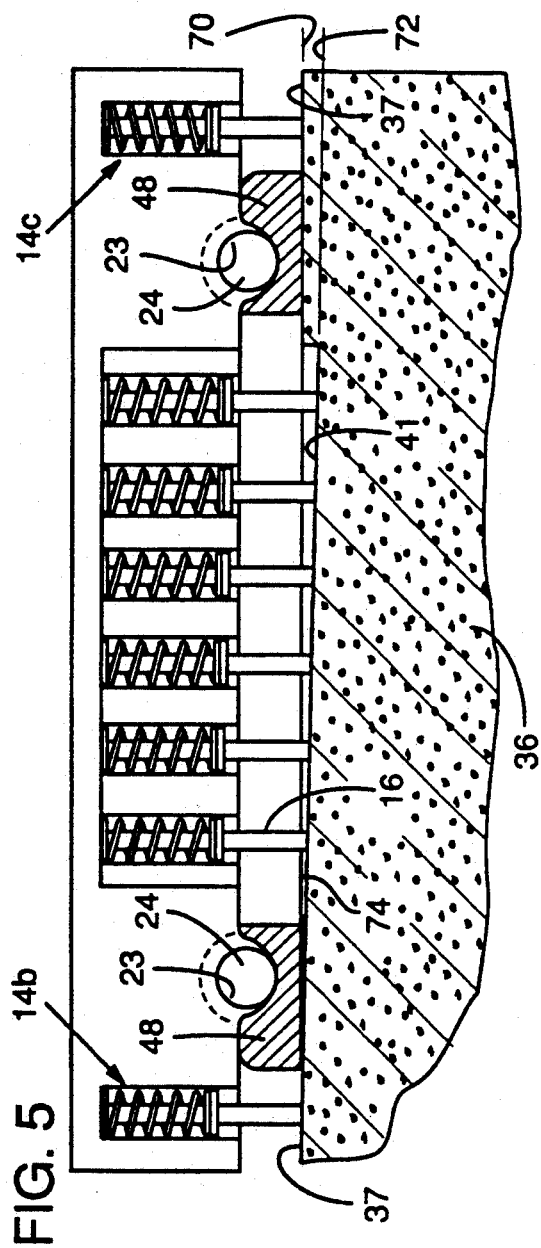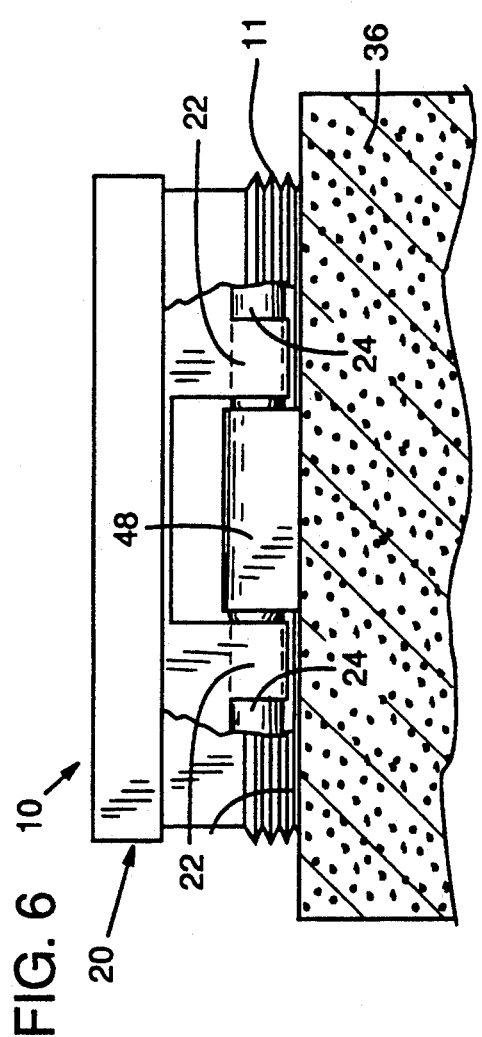

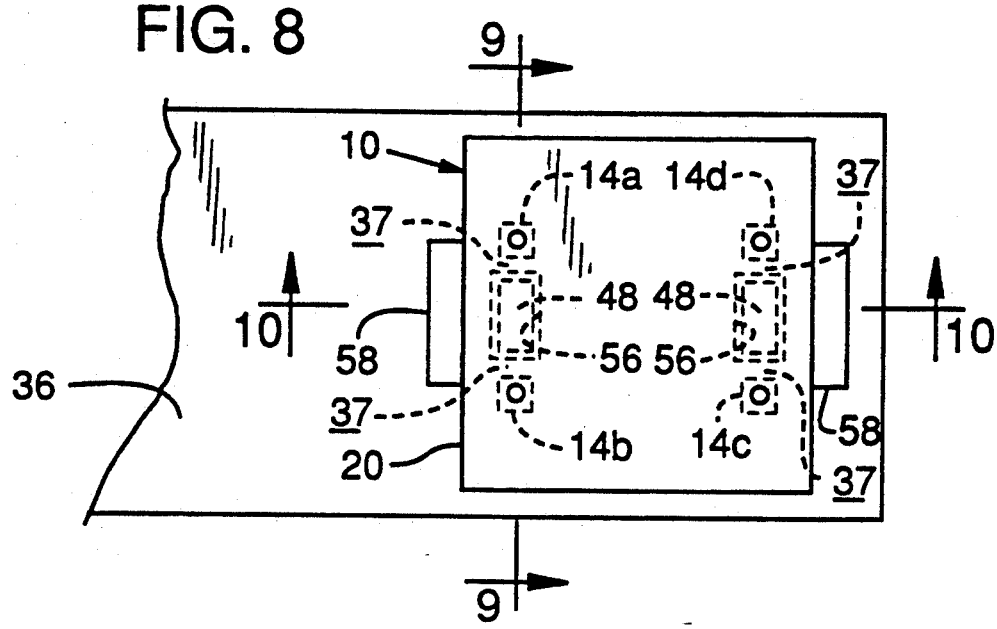
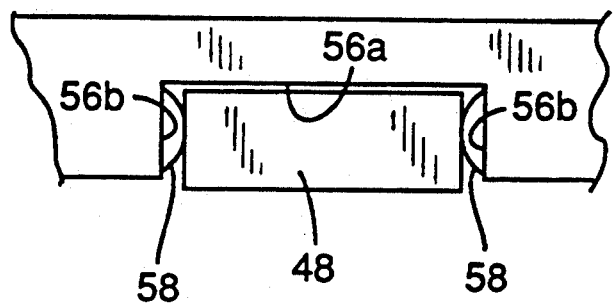
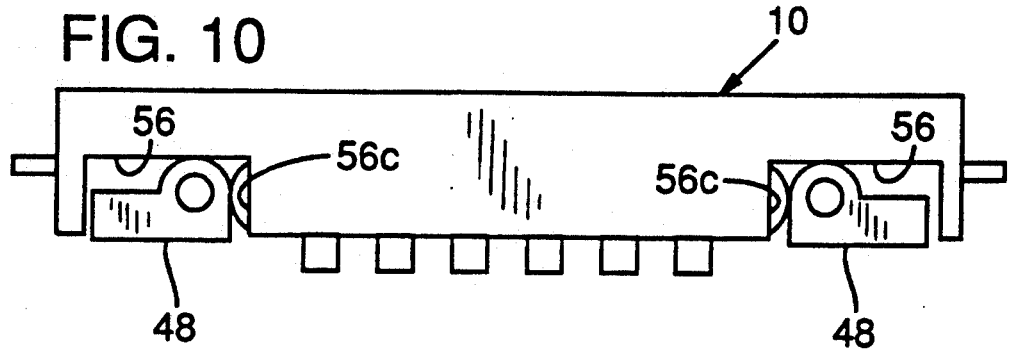

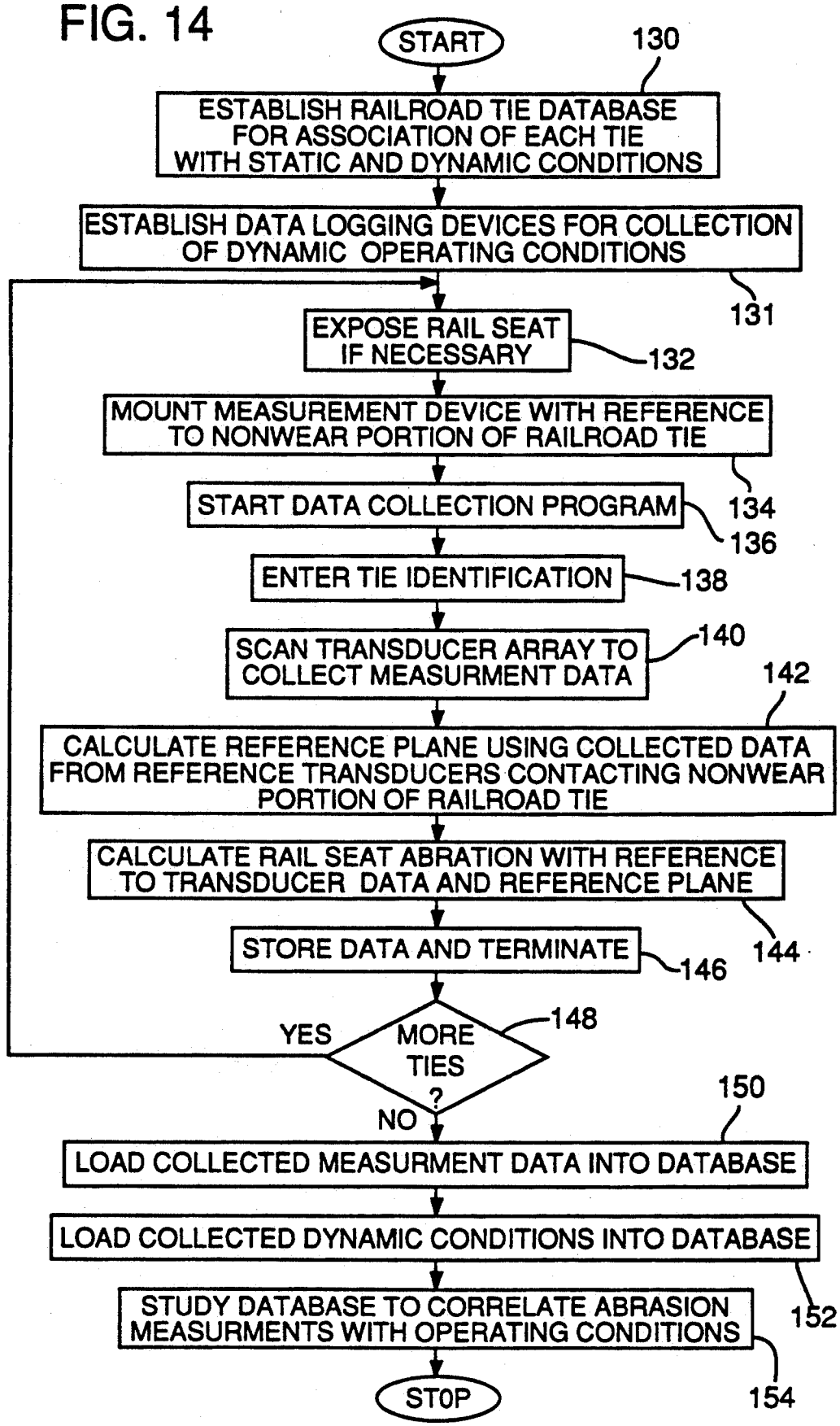

5,245,855

RAIL SEAT ABRASION MEASUREMENT

FIELD OF THE INVENTION

The present invention relates generally to railroad maintenance and particularly to wear measurement of concrete railroad ties.

BACKGROUND OF THE INVENTION

A railroad is a series of ties lying transverse to the line of train travel and a pair of steel rails lying atop the ties and along the line of train travel. Traditionally, the railroad ties have been wooden and placed in contact with the earth, but decomposition due to such earth contact has been a primary cause of wear in wooden railroad ties. Also, creosote typically used in such wood railroad ties is of environmental concern. More recently, concrete railroad ties have replaced wooden railroad ties as concrete is less affected by earth contact and, therefore, lasts longer. Additionally, the rail is easier to remove and replace when used in conjunction with concrete ties. Finally, concrete railroad ties provide a stiffer, and therefore more desirable, overall railroad track configuration.

Use of concrete railroad ties presents a different source of railroad tie wear as compared to use of wooden railroad ties. The wood-to-steel interface for a wooden tie railroad does not present as significant source of abrasion to the railroad tie as does the concrete-to-steel interface for a concrete railroad tie. In other words, wood is more resilient than concrete and better withstands the pounding forces imposed by the steel rail than does the less resilient concrete. To mount a rail upon a concrete tie, a spring fastener couples the rail and tie, and bears downward upon the rail to maintain the rail against the rail seat of the tie. A polymer pad lies between the tie and the rail to prevent direct contact between the steel of the rail and the concrete of the tie. Despite placement of such polymer pad or similar material, however, rail seat abrasion remains a problem in concrete ties.

Rail seat abrasion can significantly deteriorate the performance and dramatically shorten the life of the railroad tie. Specifically, deterioration of the rail seat can resulting in loosening of the rail from the railroad tie. The spring fastener must bias the rail against the rail seat under a specified magnitude of spring tension as a rail mounting force. When the rail seat wears, however, this affects the amount of tension in the spring fastener and the required magnitude of rail mounting force may not be achieved. For example, a typical fastening spring develops approximately 2650 pounds per square inch (psi) at the rail seat, but for every millimeter of rail seat lost to abrasion, as much as 100 psi of fastening force is lost. Ultimately this decreased holding ability of the fastener system allows the rail to slide atop and impact the concrete tie resulting in accelerated rail seat abrasion, pull-apart, and thermal misalignments.

An additional concern is that abrasion of the concrete tie surface exposes the aggregate within the tie to environmental conditions, moisture, sand and other contaminants thereby further accelerating rail seat abrasion. Finally, the abraded rail seat also forms a water collecting pocket contributing to further degradation of the concrete tie.

The problem of abrasion in concrete railroad ties has manifested itself most notably in the concrete railroad ties used in the Northwest portion of North America. Concrete railroad ties have been used in Europe for many years, but without acute rail seat abrasion. Concrete railroad tie abrasion may be due to the combined affects of the extremely high, as compared to Europe, wheel loadings commonly handled by North American railroads operating in rugged, steep mountainous areas with numerous restrictive curves. At this time, however, the causes of concrete tie abrasion are not clearly understood.

Rail seat abrasion may be related to excessive compressive stresses developed in the system which attaches the rail to the concrete tie. Another potential cause of rail seat abrasion may be moisture collecting under the polymer pad at the rail seat surface which may then be absorbed into the concrete. Repeated freezing and thawing of this absorbed water results in cracking and deterioration of the concrete structure. Other possible sources of rail seat abrasion may be particular manufacturing defects; temperature variation patterns; railroad arrangements such as curvature, grade and banking; and the nature of the pad interposed between the rail and the rail seat.

Whatever the cause of rail seat abrasion in concrete railroad ties, there exists a need to better understand the phenomenon of rail seat abrasion so that a solution and preventative measures may be taken. The fact the European railroads experience less rail seat abrasion than do North American railroads suggests that rail seat abrasion can at least be explained and predicted for preventative maintenance, and hopefully avoided altogether.

Hence, concrete rail tie abrasion, especially in North American railroads, is an area of concern to the railroad community. Careful monitoring and study will yield solutions to concrete railroad tie abrasion and thereby avoid acute deterioration of concrete railroad ties.

Measurement of concrete tie abrasion has been conducted in an attempt to monitor the wear of concrete ties and better understand the nature of such abrasion. One method of rail seat abrasion measurement is by direct manual measurement. In this method of rail seat abrasion measurement, the rail seat is exposed and a measuring frame is placed adjacent the rail seat abrasion site. More specifically, the measuring frame lies about the outer periphery of the abrasion site upon the upper surface of the tie and a dial meter is used to measure a distance from a reference point on the measuring frame to the abraded surface of the rail seat. While some form of registration of the measuring frame and rail seat has been used, this method of measurement has proven unreliable for the purpose of accurate rail seat abrasion measurement.

One major setback in such abrasion studies, therefore, has been an inability to provide reproducible abrasion measurements. In other words, a reliable method of rail seat abrasion measurement must provide the same wear measurements for a given rail seat on repeated measurements. Such reproducible abrasion measurements are essential to reliable long-term study of rail seat abrasion measurements. More particularly, in order to accurately determine the rate of rail seat abrasion, one must collect measurements of rail seat abrasion and later return, e.g. after a given period of railroad service and exposure to environmental conditions, and collect a second set of measurements for the same abrasion sites. By using a reproducible method of rail seat abrasion measurement, the amount of wear can be inferred directly from measurement differences.

A second concern with such manual rail seat abrasion measurement is the danger associated with an upraised continuous length railroad rail. More particularly, to accomplish rail seat measurement, it is necessary to expose the rail seat. Such exposure requires dismounting of the fastening system and lifting of the rail by use of a truck-jack above the rail seat. In a continuous length rail system, the rail can be raised only approximately six inches. This leaves little room at the exposed rail seat for measuring of the abrasion site. Furthermore, such upraised continuous length rails present a hazard to workers, especially if workers were required to perform manual measurement steps underneath the upraised rails. Indeed, because of the unpredictability of such upraised, continuous length rails, workers should never place their hands between an upraised rail and the rail seat. Such hazards are described in all railroad rule books.

Another problem encountered in measurement of rail seat abrasion is the need to quickly obtain measurements. Because the rail must be lifted some distance above the tie in order to expose the rail seat, the section of railroad under inspection is unavailable for train traffic during measurement activities. For this reason, any method of rail seat abrasion measurement must be not only accurate and reproducible, but also rapid in order to minimize the time during which the railroad is unavailable for service.

Accordingly, it would be desirable to provide a method of concrete tie abrasion measurement which is reproducible per individual railroad tie over long separated data collection operations in order to accurately determine the amount of rail seat abrasion. Such accurate methods of rail seat abrasion measurement will provide a better understanding of the phenomenon of rail seat abrasion in concrete ties, and therefore provide a basis for preventing or correcting the problem of rail seat abrasion in concrete ties, or at least provide a basis for predicting concrete tie longevity.

Furthermore, it is desirable that a method of rail seat abrasion measurement be rapid to avoid excess system downtime, be performed with a minimum amount of clearance between the concrete tie and the rail such that the rail need only be lifted a minimum distance above the tie, and not require workers' hands in the hazardous area between an upraised rail and the rail seat.

SUMMARY OF THE INVENTION

A method of rail seat abrasion in accordance with the present invention comprises the steps of releasing the rail and raising the rail above the railroad tie a sufficient distance to place a relatively thin measurement device against the exposed surface of the concrete rail tie. The measuring device contacts the worn portion of the concrete tie to obtain abrasion measurements and contacts non-wearing portions of the rail tie adjacent the worn portion. The non-wearing portion of the tie is taken as a reference surface from which wear is measured. In this manner, consistent and reproducible wear measurements are obtained as the non-wearing portion can be taken as unchanged from measurement to measurement.

In accordance with the preferred embodiment of the present invention, the measurement device includes an array of linear transducers having plunger pins wherein plunger pin position produces a corresponding output signal. The preferred embodiment includes a device mounting structure adapted for rapid attachment to fixed non-wearing portions of the concrete tie whereby the fixed portions of the tie provide a mounting registration reference for the measurement device. Placement of the array of transducer pins over the area of rail seat abrasion and over the non-wearing area surrounding the rail seat provides data representing the current condition of the rail seat. More particularly, those transducer pins contacting the unworn portion of the concrete tie provide a signal reference relative to the position of transducer pins contacting worn portions of the concrete tie. Data is quickly collected from the transducer array by coupling to a computer device which stores the data along with an identification of the particular concrete tie from which the data is collected.

A section of railroad track is quickly measured for rail seat abrasion by lifting the rail from the ties over a given section and moving the measurement device along each selected rail seat site while taking measurements and entering the identification of each rail tie. Data collected in this manner may be stored in the collection device for later analysis and comparison to previous or subsequent measurements of the same concrete ties. The extent of wear may then be correlated with such static information as the nature of the track, e.g. curves, bank, grade, etc., and with dynamic operational and environmental information such as load levels imposed, intervening temperature patterns and moisture conditions in order to better understand the cause of, and derive a preventative solution to, rail seat abrasion in concrete ties.

BRIEF DESCRIPTION OF THE DRAWINGS

For a better understanding of the invention, and to show how the same may be carried into effect, reference will now be made, by way of example, to the following drawings wherein like reference numerals refer to like elements:

FIG. 5 is a sectional view of the rail seat abrasion measurement device of FIG. 1 as mounted and taken along lines 5—5 of FIG. 4.

FIG. 6 is a side view of the rail seat abrasion measurement device taken along lines 6—6 of FIG. 4 and partially broken away to show mounting on the railroad tie.

FIGS. 8-10 illustrate an alternative mounting arrangement and sensor configuration for the abrasion measurement device of the present invention.

FIG. 14 is a flow chart illustrating rail seat abrasion measurement and analysis for a set of concrete railroad ties using the abrasion measurement device and data collection device of FIG. 1 and the data logging arrangement of FIG. 10.

DETAILED DESCRIPTION

Figure 1:
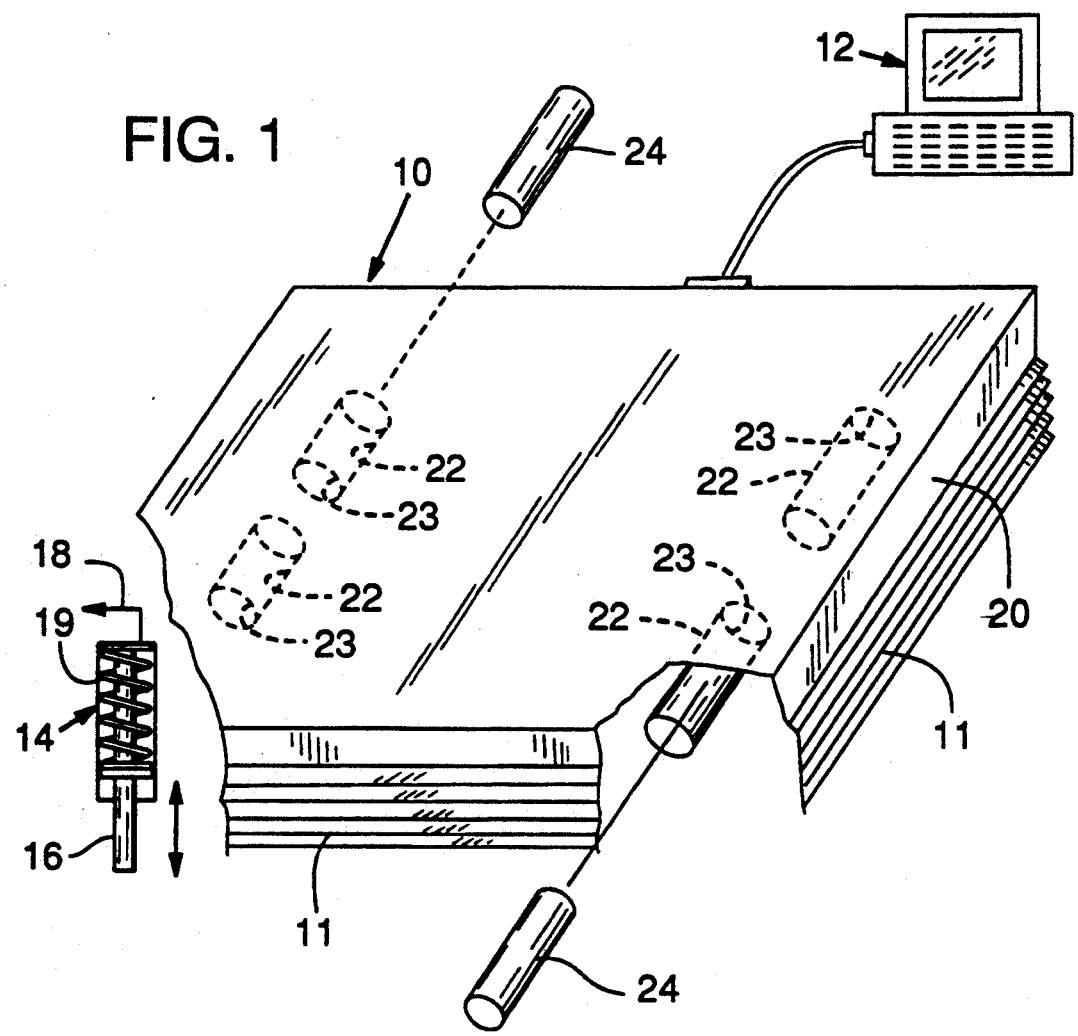
FIG. 1 is a perspective view partially broken away of a rail seat abrasion measurement device and a data collection device in accordance with the present invention.

FIG. 1 is a perspective view of a rail seat measurement device 10 and a data collection device 12, e.g., portable computer, according to a preferred embodiment of the present invention. As will be explained more fully hereafter, rail seat abrasion measurements are taken by inserting measurement device 10 between a rail seat and an upraised railroad rail. In raising the railroad rail above the rail seat, only a limited amount of clearance, e.g. six inches, is available between the rail seat and the upraised rail without significantly dismantling the railroad system at the site of measurement. Accordingly, measurement device 10 is a generally thin device, e.g., on the order of four inches, adapted to fit within a small vertical space between the upraised rail and the rail seat. The length and width dimensions of measurement device 10 generally correspond to the length and width dimensions of the rail seat to be measured, but slightly greater in order to reference non-wearing portions of the railroad ties.

Rail seat abrasion measurements are necessarily taken in situ. Accordingly, the data collection device 12 is desirably a portable battery operated device capable of suitably collecting data from measurement device 10 and storing such data for later analysis. In the preferred embodiment, data collection device 12 may be implemented as a general purpose portable computer adapted for coupling to measurement device 10 and executing data collection programs written in accordance with the present invention.

Rail seat abrasion measurement device 10 comprises a plurality of transducers 14 mounted to the body of device 10, of which one such transducer 14 is shown in the broken away portion of FIG. 1. A rubber boot 11 surrounds the lower periphery of measurement device 10 as protection for the transducers 14 at the underside of device 10. Each transducer 14 includes a vertically positionable plunger pin 16 and provides an output signal 18 corresponding to pin 16 position. The position of each plunger pin 16 is biased to a fully extended position by a spring 19 coupling the plunger pin 16 and the remainder of the transducer 14. In the illustrated embodiment, transducers 14 are linear potentiometers available from Spectrol, Inc., providing a voltage division function at output signal 18 according to pin 16 position.

Rail seat abrasion measurement device 10 further includes a registration structure 20 integral to the body of device 10. Registration structure 20 is adapted to contact a non-wearing portion of a concrete railroad tie to establish a consistent, i.e., reproducible, mounting of device 10 upon the railroad tie. In the embodiment of FIG. 1, registration structure 20 includes a pair of pin bushing members 22 on opposite sides of measurement device 10, the apertures 23 of each pair of members 22 being axially aligned. For each pair of pin bushing members 22, a support pin 24 inserts through apertures 23 to capture a railroad tie shoulder (not shown in FIG. 1) between bushing members 22. In this manner, measurement device 10 may be consistently mounted on a given pair of railroad tie shoulders and thereby provide consistent output signals 18 for repeated mounting of device 10 thereon. Accordingly, when measuring rail seat abrasion over a period of time, a difference in each output signal 18 may be properly interpreted as rail seat abrasion rather than a measurement error associated with inconsistent mounting of device 10 upon a given railroad tie.

Figure 2:
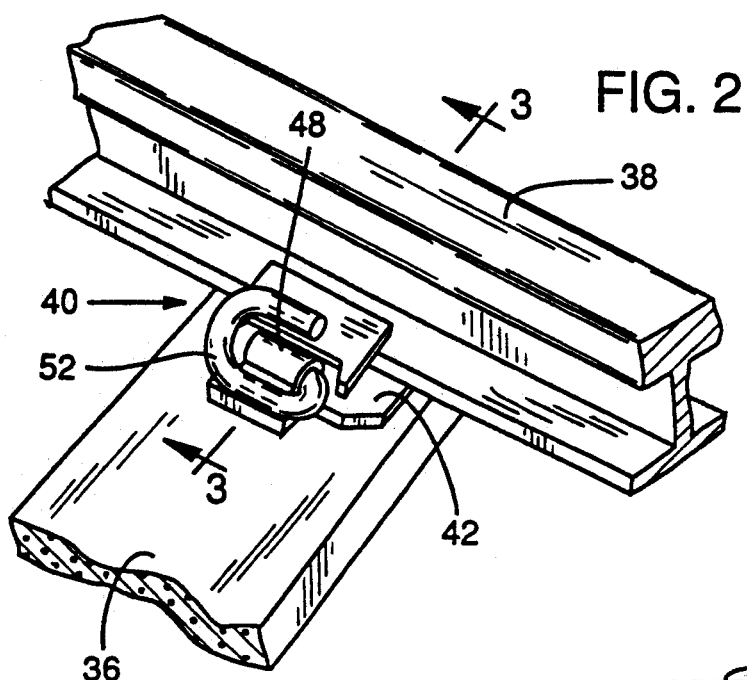
FIG. 2 is a perspective view of a concrete tie, a steel rail, and the fastener assembly used to maintain the rail upon the rail seat.
Figure 3:
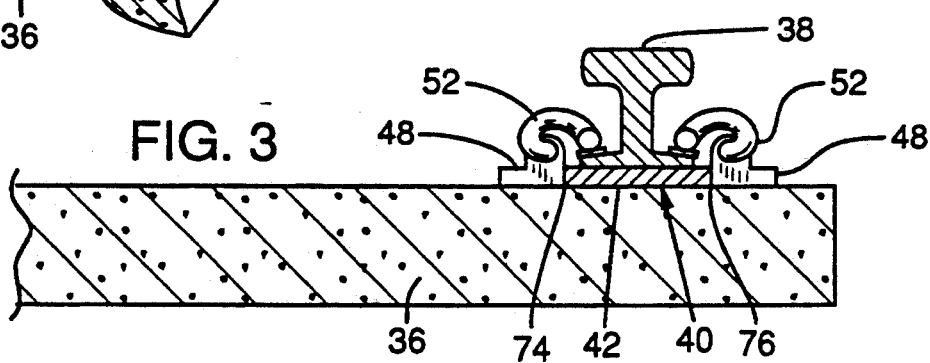
FIG. 3 is a sectional view taken along lines 3—3 of FIG. 2, showing the rail, fastener and tie assembly.

FIG. 2 is a perspective view of a rail seat for which the FIG. 1 embodiment of the present invention is adapted to provide abrasion measurement. It should be apparent, however, that the present invention may be practiced for other types of rail seat configurations. FIG. 3 is a sectional view of the rail seat of FIG. 2 taken along lines 3—3 of FIG. 2. In FIGS. 2 and 3, a concrete railroad tie 36 lies perpendicular to a steel railroad rail 38. Railroad tie 36 supports railroad rail 38 from below at the subject rail seat 40 of concrete railroad tie 36. A polymer pad 42 lies between rail seat 40 and rail 38 as a precaution against excessive wear otherwise resulting from direct contact between the steel of rail 38 and the concrete of tie 36. Despite use of such polymer pad, however, significant abrasion at rail seat 40 can occur.

Lying along the length of tie 36 and on each side of rail seat 40 are a pair of shoulders 48 integrally attached to tie 36. Each shoulder 48 includes an aperture 50 through which an end portion of a fastening spring 52 inserts for coupling to tie 36. The opposite end of spring 52 bears downward against the base of rail 38, by way of a spring contacting plate 54, in order to capture rail 38 against polymer pad 42. The opposite end of railroad tie 36 (not shown) includes a similar pair of shoulders 48 and fastening springs 52 as a mounting arrangement for the opposite rail supported by concrete tie 36.

Figure 4:
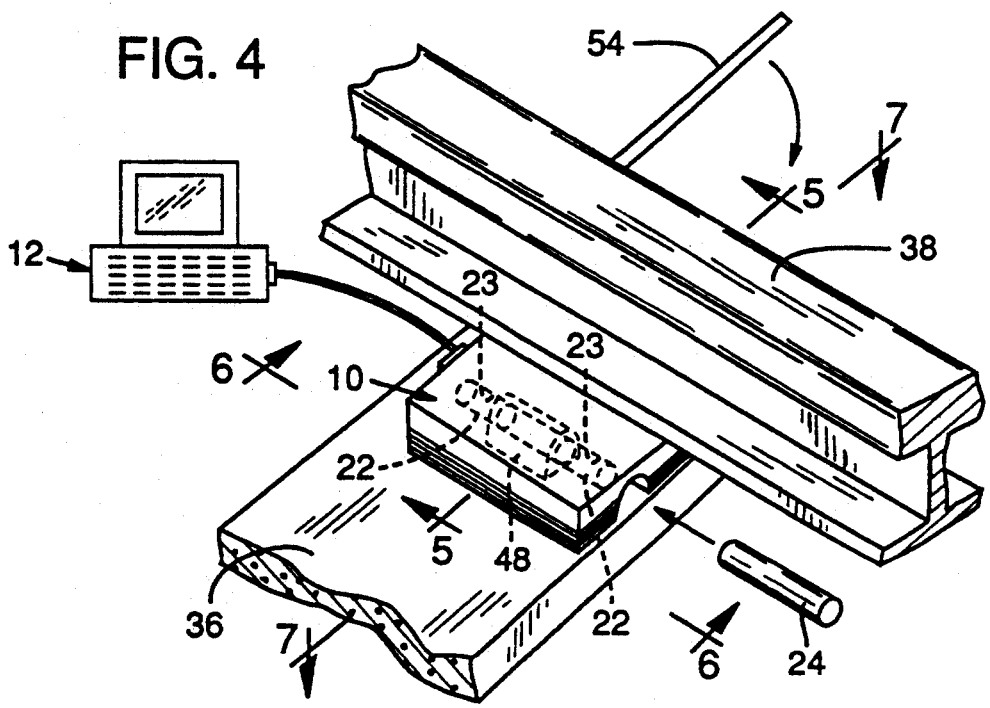
FIG. 4 illustrates a rail detached and lifted away from the tie for placement of the measurement device on the rail seat in order to collect abrasion data by means of a data collection device.

FIG. 4 illustrates raising of rail 38 above railroad tie 36 and placement of the measuring device 10 at the rail seat 40. In FIG. 4, springs 52 have been removed from shoulders 48 whereby rail 38 may be raised approximately six inches above rail seat 40 by use of lever bar 54. Once rail 38 is raised above rail seat 40, polymer pad 42 is removed to expose rail seat 40 for measurement. At this time, the rail seat 40 and the surrounding surface of tie 36 should be cleaned as by compressed air, brushing, or in some cases light sand blasting. Measurement device 10 is then interposed in the vertical space between rail 38 and rail seat 40 for mounting upon the shoulders 48. More particularly, the pin bushing members 22 on each side of measurement device 10 are positioned to capture therebetween the corresponding shoulder 48. The aperture 50 of each shoulder 48 is aligned with the aperture 23 of each pair of axially aligned pin bushing members 22. In such arrangement, a support pin 24 may be inserted through the corresponding pin bushing members 22 and shoulder 48 to secure measurement device 10 upon the concrete tie 36.

The plunger pin 16 of each transducer 14 (FIG. 1) of measurement device 10 desirably extends past the range of maximum rail seat 40 abrasion whereby such mounting of rail seat abrasion measurement device 10 compresses each pin 16 at least to some extent upon mounting upon tie 36.

FIG. 5 is a sectional view of the rail seat measurement device taken along lines 5—5 of FIG. 4, and FIG. 6 is a side view partially cut away of the device 10 taken along lines 6—6 of FIG. 4. In FIGS. 5 and 6, measurement device 10 is supported on each side by the pair of pin bushing members 22 and support pins 24 as coupled to the shoulders 48. Shoulders 48 represent a stable non-wear portion of concrete tie 36, measurement device 10 thereby consistently mounts upon each concrete tie 36 regardless of the amount of rail seat abrasion and regardless of individual differences between shoulder 48 mountings on different ties 36. It may be appreciated, therefore, that such mounting arrangement of measurement device 10 represents a reproducible mounting arrangement per individual concrete tie 36. In other words, despite individual variations between each concrete tie 36, device 10 consistently remounts upon a given railroad tie 36 to provide reliable abrasion measurements.

Figure 7:
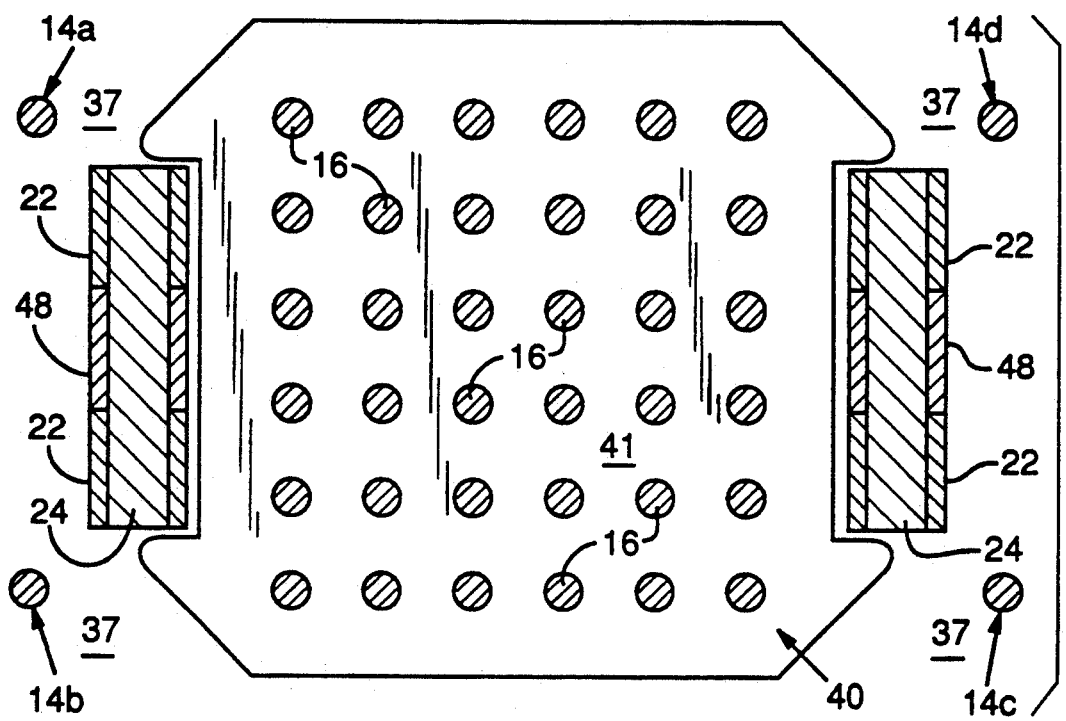
FIG. 7 is a sectional view of the device as mounted and taken along lines 7—7 of FIG. 4 to show plunger pin contact points.

FIG. 7 is a sectional view of the measurement device 10 as taken along lines 7—7 of FIG. 4. In FIG. 7, bushing members 22 of device 10 rest on corresponding ones of support pins 24 which, in turn, rest upon the shoulders 48 of concrete railroad tie 36. The transducers 14 are distributed across the rail seat 40 in such manner to direct plunger pins 16 against the abraded surface 41 of rail seat 40. Generally, the abraded surface 41 corresponds in shape to that of the polymer pad 42. As seen in FIG. 7, a 6×6 array of transducers 14 provides sufficient measurement data for characterizing the abraded surface 41 of rail seat 40. Also, reference transducers 14a-14d are positioned to extend downward and contact the non-wear surface 37 of concrete tie 36. Accordingly, signals taken from reference transducers 14a-14d provide a basis for interpreting signals taken from the remainder of the transducers 14. More particularly, the signals taken from reference transducers 14a-14d establish a non-wear plane corresponding to the surface 37 of tie 36. Signals taken from the remaining transducers 14 then may be zeroed relative to the non-wear plane as derived from signals taken from transducers 14a-14d.

FIGS. 8-10 illustrate an alternative mounting structure 20 for the measurement device 10. In FIGS. 8-10, the measurement device 10 is provided with a mounting structure 20 having slot formations 56 adapted to fit closely over the shoulders 48. Measurement device 10 is further provided with a pair of handles 58 on each side of measurement device 10. The ceiling or upper surface 56a (FIG. 9) of each slot formation 56 rests directly on the top of the corresponding shoulder 48. The end portions 56b of each slot formation 56 include spring clips 58 each coupling the mounting structure 20 to the shoulder 48 to capture the shoulder 48 centrally within the slot formation 56. The inside surface 56c (FIG. 10) of each slot formation 56 includes a spring clip 58 bearing against the corresponding shoulder 48 for capturing the measurement device 10 centrally between the pair of shoulders 48. In use of the measurement device 10 shown in FIGS. 8-10, a user inserts the device between an upper raised rail 38 and the rail seat 40. By gripping the handles 58 to bear downward on the device 10 to bring the ceiling surface 56a of each slot formation 56 against the top of the corresponding shoulder 48, the measuring device 10 is brought into position for obtaining measurement data from transducers 14. Because a support pin is not used in the embodiment of FIGS. 8-10, the reference transducers 14a-14d may be more closely positioned adjacent the non-wearing surface 37 of railroad tie 36. More particularly, the reference transducers may be positioned close to the abraded surface 41 and near shoulders 48.

Figure 11:
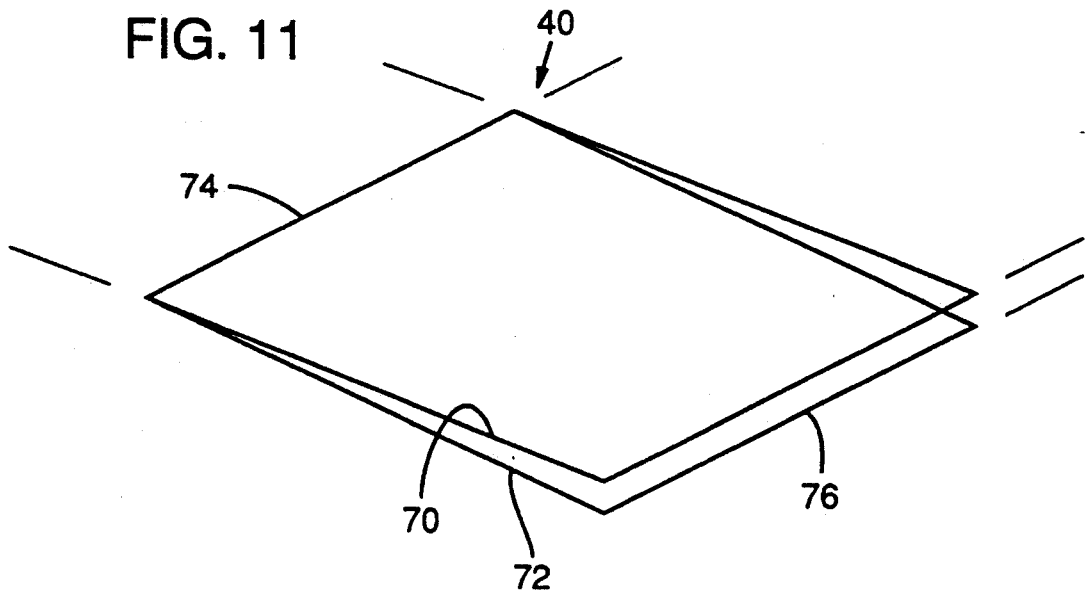
FIG. 11 is a block diagram of a typical wear pattern for a concrete rail tie as determined by the rail seat abrasion measurement device of FIG. 1.

FIG. 11 illustrates a typical wear pattern for a concrete railroad tie 36. The orientation of the wear pattern illustrated in FIG. 11 is indicated in FIGS. 5 and 7. In FIGS. 5, 7 and 11, a non-wear wear plane 70 corresponds to the condition of an unworn rail seat 40, i.e., the surface 37 (FIG. 7). An abrasion plane 72 corresponds to the abraded surface 41 of an abraded rail seat 40. The abrasion plane 72 is typically inclined relative to the non-wear plane 70. More particularly, the inside edge 74 of rail seat 40 typically experiences less abrasion than does the outside edge 76 of rail seat 40. A typical depth of minimum abrasion at outside edge 76 is approximately two to three millimeters and extreme measurements are approximately 12 mm ($\frac{1}{2}$") in depth. In some limited cases, severe degradation of concrete railroad ties has resulted in measurement of $\frac{3}{4}$ inch abrasions.

Figure 12:
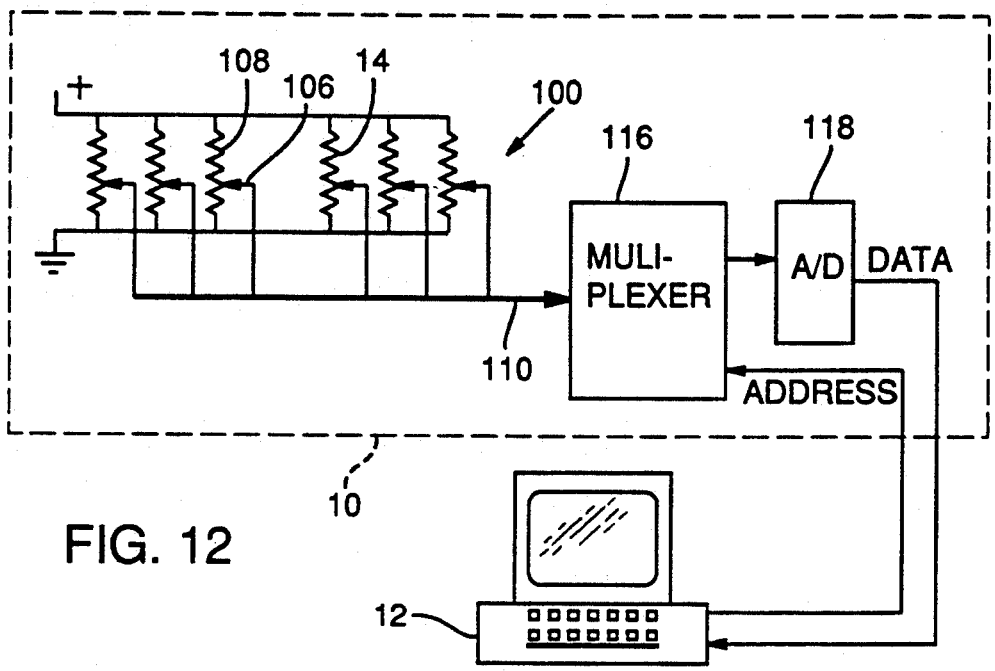
FIG. 12 is a schematic illustration of the rail seat abrasion measurement device and the data collection device of FIG. 1.

FIG. 12 is a block diagram of the measurement device 10 and data collection device 12 illustrating the method of data collection from device 10. In FIG. 12, a transducer array 100 comprises the individual transducers 14, including reference transducers 14a-14d, arranged as voltage dividers coupled between a voltage source 102 and ground reference 104. Each transducer 14 has a wiper element 106 movable along the resistive portion 108 of transducer 14. Each wiper element 106 in turn couples to a corresponding conductor of a multiconductor cable 110. Accordingly, for n transducers 14, conductor 110 carries n voltage signals from transducer array 100 to an analog multiplexor circuit 116. Multiplexor circuit 116 is addressed to route the voltage present on individual conductors of multiconductor cable 110 to an analog to digital converter 118 for presentation to data collection device 12.

In the preferred embodiment, the transducer array 100 resides in the body of the illustrated measurement device 10 and the multiplexor 116 and analog to digital converter 118 comprise a bus mounted board for the portable computer operating as the data collection device 12. The board comprising the multiplexor 116 and 118 is available under the trade name AIBPC by Sunset Laboratories of Forest Grove, Or. Each such board provides eight multiplexed analog channels, and for a larger transducer array 100, several such boards may be suitably combined to provide a separate channel for each transducer 14 in array 100.

In arranging the transducer array 100 upon the body of measurement device 10, recall that the transducers 14a-14d contact non-wearing portions, i.e. surface 37, of railroad ties 36. Voltage signals taken from such transducers may be taken as a reference to account for variations in the magnitude of voltage supply 102. Voltage signals taken from such reference transducers 14a-14d should correspond to the plane 70 of FIG. 7, i.e., to the unworn surface 37 of the concrete railroad tie 36. Voltage signals taken from the remaining transducers 14, i.e., those contacting the abraded surface 41 of rail seat 40 may be zeroed or offset by the magnitude of the signals taken from the reference transducers 14a-14d.

Figure 13:
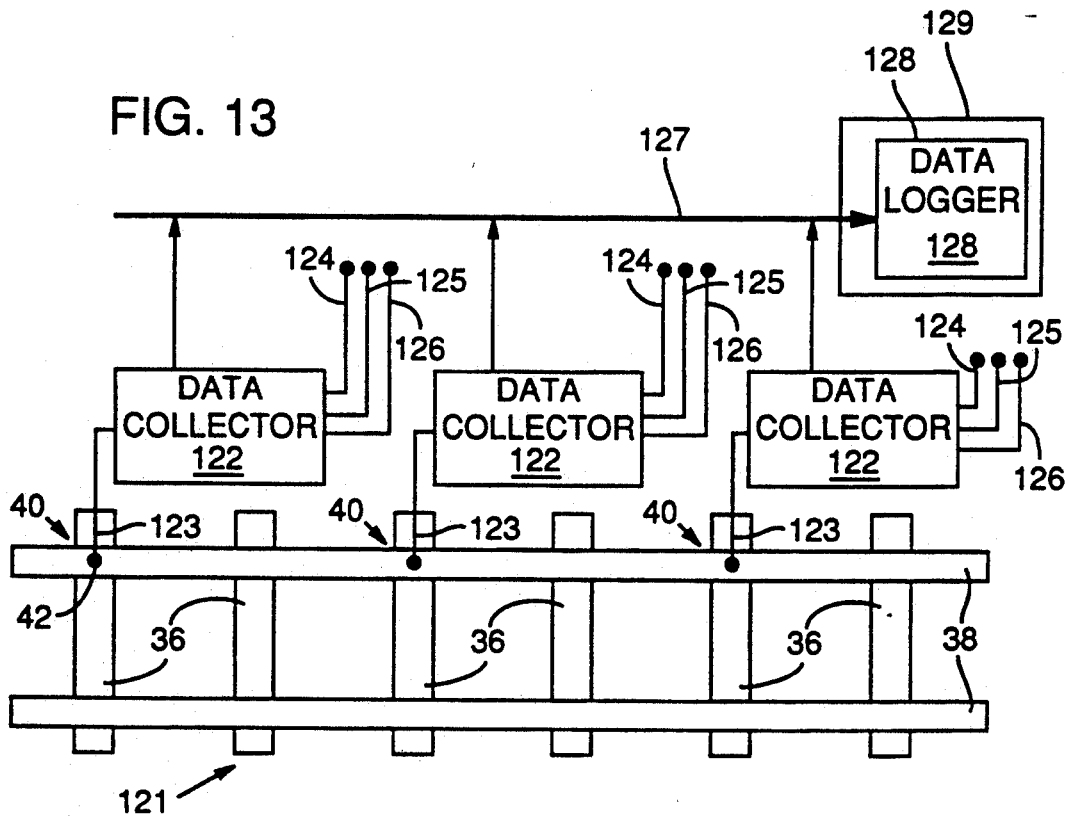
FIG. 13 illustrates a method of logging dynamic operating conditions possibly affecting rail seat abrasion in concrete railroad ties.

FIG. 13 illustrates a method of logging various dynamic environmental conditions to which rail seats are exposed for the purpose of correlating abrasion of selected rail seats 40 to such dynamic conditions. In FIG. 13, a number of ambient condition data collection devices 122 are distributed along a railroad section 121. Each data collection device 122 includes a variety of ambient condition sensors for collecting over time the environmental conditions under which rail seat abrasion occurs. For example, each data collection device 122 may include an atmospheric temperature sensor 124, a moisture detector 125 and rain gauge 126. Within each polymer pad 42 a temperature sensor 123 is imbedded and coupled to the corresponding collection device for the purpose of monitoring temperatures directly at the rail seat 40. In the illustrated embodiment, the temperature sensor 123 is implemented using an AD590 temperature sensor providing 1.0 mA of current per degree Kelvin. Such sensors are approximately the size of a paper match and suitably incorporated into the polymer pad 42.

Each data collection device 122 constantly monitors the information collected by way of sensors 123-126 and delivers such information by way of a communication link 127 to a data logging device 128 operating within a nearby railroad maintenance shack 129. Logging device thereby maintains a representation, i.e., conditions over time, of environmental conditions to which each seat 40 is exposed. Data logging device 128 is accessed periodically to collect the various data pertaining to rail seat 40 environmental conditions.

FIG. 14 is a flow chart of the overall process for measurement and analysis of rail seat abrasion according to the present invention. In FIG. 10, beginning in step 130 a database of rail ties is established for associating individual rail ties with their location, and tie type as well as various static and dynamic operating conditions. For example, each railroad tie 36 under observation is provided with a unique identification as a record key to the database and such records include an identification of the manufacturer and general configuration of the railroad tie 36 along with static operating conditions such as the curvature, bank and grade of the railroad in the vicinity of the associated rail seat and any other aspect of the railroad system which may be considered pertinent to rail seat abrasion. Continuing to step 131, once a set of railroad ties 36 are identified for study and the corresponding database established, the data logging system illustrated in FIG. 10 may be established to collect additional dynamic environmental and operational information possibly pertinent to rail seat abrasion.

The process of rail seat abrasion measurement begins in step 132 where the rail seat 40 is exposed by detaching and lifting the rail 38. Continuing to step 134, the measurement device 10 is mounted to the rail seat by referencing the shoulders 48 surrounding the rail seat. In step 136, a rail seat abrasion measurement program of data collection device 12 is initiated. In step 138, the program of device 12 first requests the user enter the tie identification key and a date. Continuing to step 140, the program then scans the transducer array 100 to collect the necessary data from the measurement device 10 in order to establish a current condition of the subject rail seat 40. In step 142, data collection device 12 calculates the reference plane using the collected data from the reference transducers contacting the non-wear portion of the railroad tie. Continuing to step 144, the data collection device 12 then calculates rail seat abrasion with reference to transducers contacting the worn portion of the rail seat 40 and with reference to the calculated reference plane from step 142. It may be appreciated that the calculation steps 142 and 144 may be postponed as the raw data taken from the transducer array may be stored for later use.

In block 146, the program operating on device 12 stores the collected transducer data and calculated data in association with the specified tie identification and date and then terminates. In decision step 148, the user may desire to take additional rail seat measurements. If additional measurements are desired, the process returns to step 132 for subsequent rail seat abrasion measurement steps on other rail seats 40. Eventually, all the subject rail seats 40 are measured and the current condition of each rail seat is stored in the data collection device 12 in association with its identification. Continuing to step 150, the data collected in and calculated by device 12 may then be incorporated into the database established in step 130. The steps 132-144 are repeated several times following intervals of rail service and exposure to environmental conditions whereby the database eventually includes several rail seat abrasion measurements, separated over time, for each rail seat 40. In step 152, additional information is loaded into the database including environmental data provided by data logging device 128 as well as load conditions on the rail system such as the frequency of use and weight of rail vehicles traversing each rail seat 40. In step 154, the database is referenced to correlate a progression of rail seat abrasion over time and operating conditions in order to better understand the nature of rail seat abrasion in concrete railroad ties.

It will be appreciated that the present invention is not restricted to the particular embodiments that have been described and illustrated, and that variations may be made therein without departing from the scope of the invention as found in the appended claims and equivalents thereof. For example, while two forms of mounting structures have been shown for the measurement device 10, it should be apparent that other mounting arrangements are possible for providing physical registration of the measurement device 10 upon non-wear portions of the railroad ties. Also, it may be appreciated that the present invention is not limited to consideration of the specifically enumerated static and dynamic operational conditions considered pertinent to rail seat abrasion. Other factors may be introduced into the method of rail seat abrasion analysis to facilitate an understanding of abrasion in concrete railroad ties.

We claim:

1. A method of measuring concrete tie rail seat abrasion in a railroad system, the method comprising the steps:

detaching a rail from a tie at the rail seat;
   lifting the rail to expose the rail seat; and
   placing an electronic measurement device at the rail seat with a reference portion of the device contacting a non-wear portion of the tie and a transducer portion of the device contacting a wear portion of the tie whereby the measurement device provides an electronic representation of the wear portion of the tie relative to the non-wear portion of the tie.

2. A method according to claim 1 wherein said method further comprises storing said representation of the wear portion of the tie in association with an identification of the tie at which the measurement was taken.

3. A method according to claim 2 wherein said method further comprises the steps:

lowering the rail and attaching the rail at the rail seat;
   using the railroad system over a given period of time;
   repeating the steps of detaching, lifting, and placing to obtain a second electronic representation of the wear portion relative to the non-wear portion; and
   comparing the first representation with the second representation to characterize wear in the rail seat over the given period of time.

4. A method according to claim 1 wherein the non-wear portion includes a portion of a rail mounting assembly adjacent the rail seat and provides a mounting registration site for the measurement device.

5. A method according to claim 1 wherein the non-wear portion includes a non-wear surface at the tie also contacted by the transducer portion of the device as a signal reference for signals taken from the transducer portion contacting the wear portion of the tie.

6. A method according to claim 1 wherein said reference portion of the device is mounted to the non-wear portion of the tie.

7. A method of characterizing rail seat wear in a plurality of concrete rail ties comprising a railroad system, the method comprising the steps:
   maintaining by information storage a representation of said plurality of concrete railroad ties and associating an identification of each tie with operating conditions;
   obtaining for each of said railroad ties a spacial measurement of a wear portion of the rail seat relative to a non-wear portion and associating each spacial measurement with the tie identification;
   incorporating the spacial measurement of each wear portion of each rail seat into said representation using the tie identification to associate each spacial measurement with the corresponding operating conditions;
   using the rail system over a given period of time;
   recording operating conditions to which at least some of said plurality of railroad ties are exposed over said given period of time;
   incorporating the recorded operating conditions into said representation in association with the identification of the corresponding railroad ties;
   repeating the steps of obtaining and incorporating to collect within said representation further of said spacial measurements in association with the corresponding rail tie identification; and
   characterizing rail seat abrasion over said given period of time as correlated to operating condition by reference to said representation.

8. A method according to claim 7 wherein the operating conditions associated with each railroad tie includes at least one of frequency of use by rail system vehicle, weight of rail system vehicles passing over, grade of rail system, curvature of rail system at rail seat, and bank of rail system at rail seat.

9. A method according to claim 7 wherein the operating conditions associated with each railroad tie includes at least one of temperature, moisture, and loading conditions.

10. A method according to claim 7 wherein said step of obtaining for each of said railroad ties a spacial measurement of a wear portion of the rail seat relative to a non-wear portion comprises the steps:
    detaching the rail from the tie at the rail seat;
    lifting the rail to expose the rail seat; and
    placing an electronic measurement device at the rail seat with a reference portion of the device contacting a non-wear portion of the tie and a transducer portion of the device contacting a wear portion of the tie whereby the measurement device provides an electronic representation of the wear portion of the tie relative to the non-wear portion of the tie.

11. An apparatus for measuring rail seat abrasion in a concrete railroad tie, the apparatus comprising:
    mounting means adapted for mounting said apparatus to a non-wear portion of said concrete tie; and
    transducer means having a movable sensor means adapted to contact the railroad tie and provide a representation of sensor means position relative to said mounting means.

12. An apparatus according to claim 11 wherein said mounting means comprises means for mounting relative to shoulder members integrally attached to said concrete tie.

13. An apparatus for measuring rail seat abrasion in a concrete railroad tie, the apparatus comprising:
    mounting means adapted for mounting said apparatus to a non-wear portion of said concrete tie; and
    transducer means having a movable sensor means adapted to contact the railroad tie and provide a representation of sensor means position relative to said mounting means, said sensor means comprising an array of movable pin elements wherein at least one of said pin elements contacts the rail seat.

14. An apparatus according to claim 13 wherein each pin element couples to the movable portion of the corresponding transducer element of said transducer means whereby each transducer produces an output signal corresponding to pin position.

15. An apparatus according to claim 13 wherein some of said pin elements are adapted to contact non-wear portions of said railroad tie whereby a corresponding output signal therefrom provides a zero reference for output signals corresponding to pin elements contacting said rail seat.

* * * * *